United States Patent [19]

Gordon

[11] 4,184,255
[45] Jan. 22, 1980

[54] APPARATUS FOR AND METHOD OF FORMING ACCURATE HINGE AXIS TOOTH POSITIONERS

[76] Inventor: Woodford W. Gordon, 945 Corbett Ave. #309, San Francisco, Calif. 94131

[21] Appl. No.: 803,221

[22] Filed: Jun. 3, 1977

[51] Int. Cl.² ............................................... A61C 7/00
[52] U.S. Cl. ............................................ 433/6; 433/49
[58] Field of Search ............ 32/14 C, 14 B, 32, 40 R; 425/180, DIG. 11, DIG. 29, 406, 411; 249/54; 128/136; 269/254 DF

[56] References Cited

U.S. PATENT DOCUMENTS

| 250,513 | 12/1881 | Finney | 425/180 |
|---|---|---|---|
| 279,365 | 6/1883 | Evans | 425/180 |
| 283,487 | 8/1883 | Housel | 425/180 |
| 1,502,377 | 7/1924 | Davies | 269/254 DF |
| 1,537,884 | 5/1925 | Romine et al. | 269/254 DF |
| 2,467,432 | 4/1949 | Kesling | 32/14 B |
| 2,545,249 | 3/1951 | Ackerman | 32/32 |
| 2,775,036 | 12/1956 | Kesling | 32/14 B |
| 3,089,487 | 5/1963 | Enicks et al. | 128/136 |
| 3,429,045 | 2/1969 | Anderson et al. | 128/136 |
| 3,576,075 | 4/1971 | Scott | 32/32 |

Primary Examiner—Louis G. Mancene
Assistant Examiner—John J. Wilson
Attorney, Agent, or Firm—Robert Charles Hill

[57] ABSTRACT

An apparatus for and method of forming accurate hinge axis tooth positioners prepares models of the upper and lower teeth of a patient with the teeth relocated to predetermined positions, takes an interocclusal record of the prepared models mounted on an articulator in the occlusal position but spaced apart the thickness of the tooth positioner material, duplicates the models and mounts them on a correlator in indexed engagement with the interocclusal record, removes the interocclusal record from between the duplicated models and substitutes therein a resilient deformable material, returns the duplicated models to the established interocclusal record position to form impressions of the teeth in the material, and cures the material through the application of heat.

4 Claims, 7 Drawing Figures

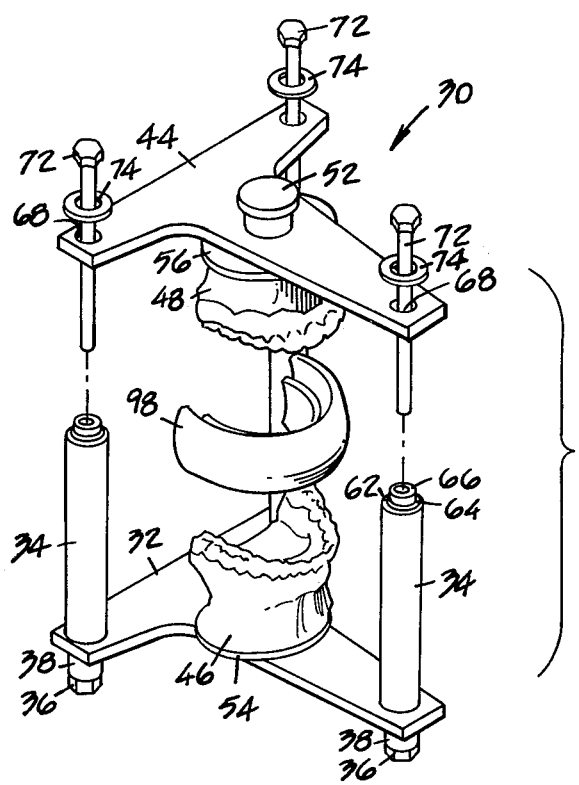
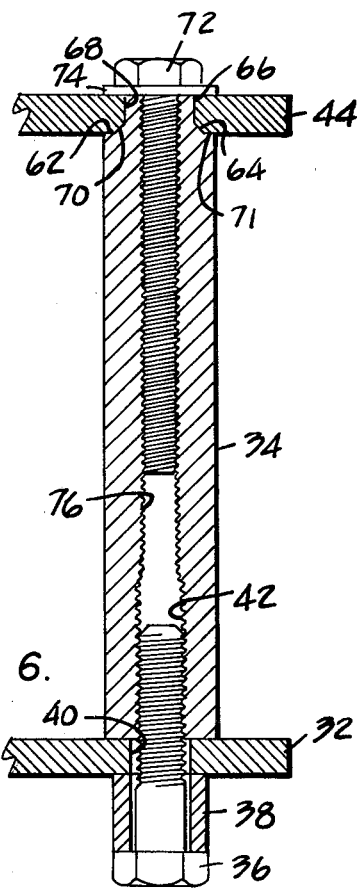
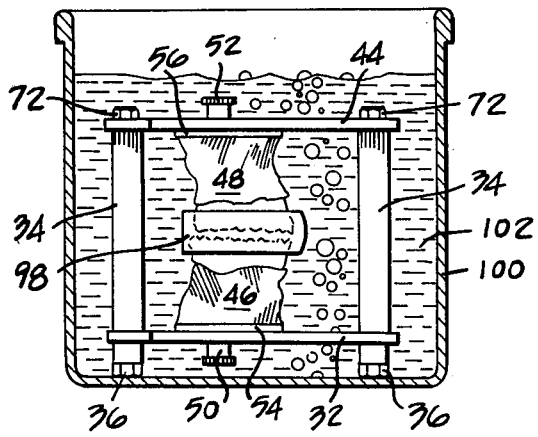
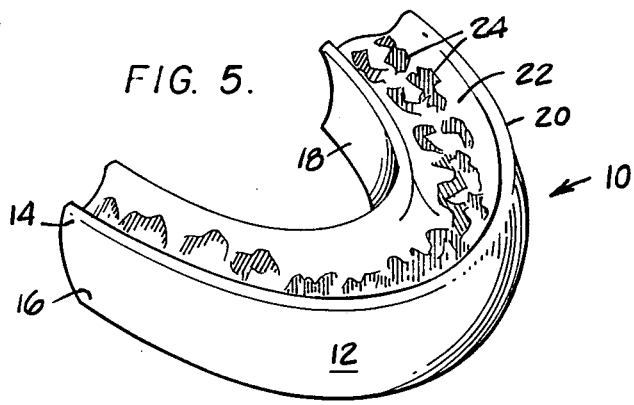

APPARATUS FOR AND METHOD OF FORMING ACCURATE HINGE AXIS TOOTH POSITIONERS

SUMMARY OF THE INVENTION

An apparatus for and method of forming accurate hinge axis tooth positioners duplicates in the positioner that exact relationship between the opposing set-up models on the articulator as evidenced by the interocclusal record.

BACKGROUND OF THE INVENTION

The present invention relates generally to means for and method of forming dental devices, and more particularly to a correlator in which a tooth positioner is formed and to the method of forming the tooth positioner by employment of the correlator.

The present novel correlator and the method of employing it to make an accurate hinge axis tooth positioner affords an efficient and reliable apparatus for and method of forming tooth positioners which is radically different from anything heretofore found in the dental art.

A tooth positioner is adapted to surround the teeth of a wearer for directing the teeth towards the assumption of preselected ideal positions, especially for the final artistic positioning and retention of the teeth in cases that have already had basic treatment completed with other applicances, such as bands and/or wires.

Heretofore, positioners have generally been made according to U.S. Pat. No. 2 775 036 wherein soft vulcanizable rubber of suitable formula is placed within a dental flask and exposed to high heat and pressure in order to become permanently formed with the teeth impressions of the models. Unfortunately, this process, although long accepted, never produced an accurate positioner because tilt and torque were always present due to an excess of rubber material in the flask which results in "flashing" as the excess material forces its way out of the flask because it expands with temperature. The flashing could not be avoided even with tons of pressure exerted on the flask. If too little rubber was put into the flask, the flashing would be eliminated but the positioner would not be completely formed because of lack of material.

All other positioner techniques require flasking which always results in unwanted excess of material between the flask opening while packing or processing, which will change the interocclusal wedge opening of the material. This improper wedge will tend to subluxate the condyles from the fossae as the patient reaches forward just to seat into the positioner, which makes it hard to wear and will cause adverse tooth movements if worn for an extended period of time.

The present invention incorporates the only known method processing a tooth positioner without flasking and will reproduce the same exact opening from the articulated set-up models without any excess of material.

Objects of the Invention

It is the primary object of the present invention to provide a new and improved apparatus for and method of forming accurate hinge axis tooth positioners.

Another object is to provide a novel centric correlator for forming the tooth positioner which achieves accurate results, is sturdy in construction and can be readily used by dental or laboratory personnel.

A further object of the invention is to provide a process wherein a tooth positioner can be fabricated with absolutely no flashing.

A still further object is to provide a method and apparatus which is inexpensive to manufacture and long lasting in usage.

A final object is to provide a method and apparatus which provides a tooth positioner which coincides with the exact hinge axis closure of the patient.

BRIEF DESCRIPTION OF THE DRAWINGS

FIG. 3 is a perspective view showing the positioner material between the duplicated models.

FIG. 4 is a side view showing the positioner material being cured by boiling water.

FIG. 5 is a perspective view illustrating an accurate hinge axis tooth positioner constructed in accordance with the present invention.

FIG. 6 is a sectional view of one of the upright posts of the correlator shown in FIG. 1.

DESCRIPTION OF THE PREFERRED EMBODIMENT

Figure 1:
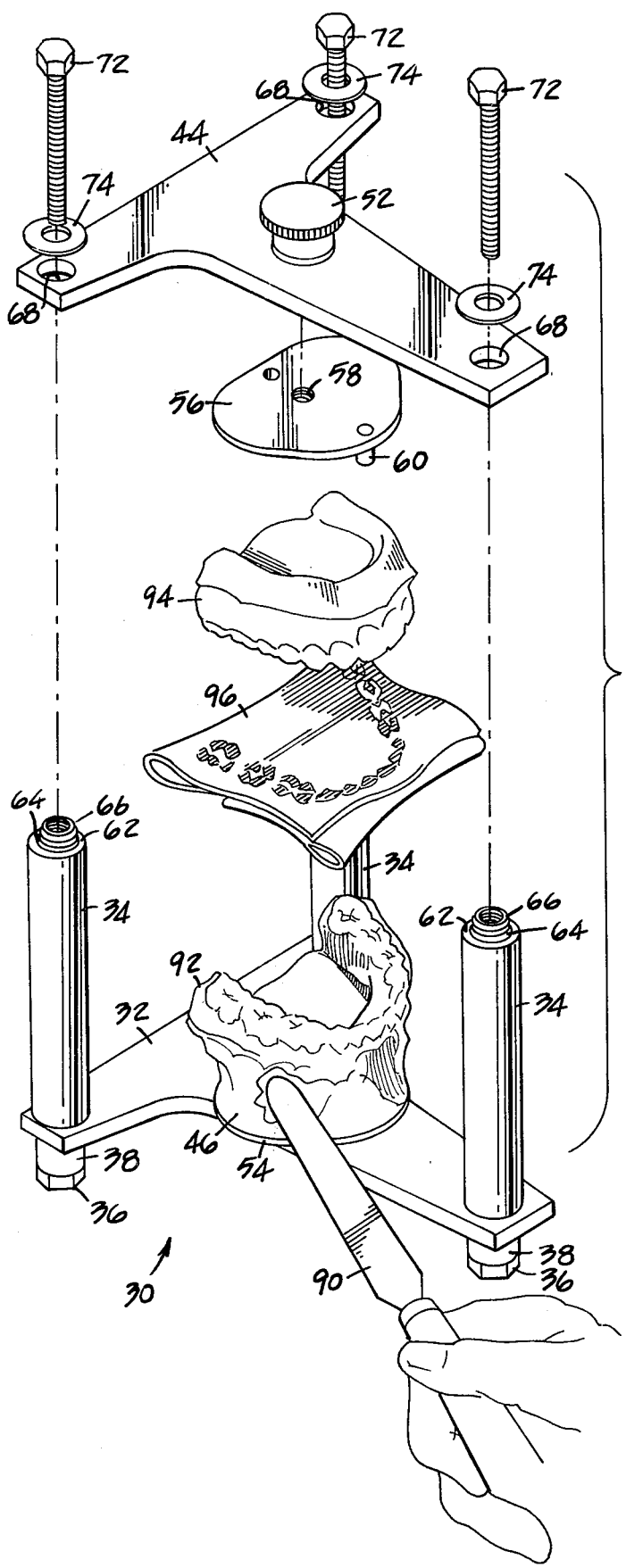
FIG. 1 is an exploded perspective view of the centric correlator illustrating the interocclusal record between the duplicated models.

Referring to FIG. 5 which illustrates the accurate hinge axis tooth positioner of the present invention, the tooth positioner generally indicated 10 has a body 12 of resilient deformable material such as a silicone type rubber tooth positioning material available from Oral Arts Orthodontic Laboratory, Inc., 1310 Old Bayshore Highway, Burlingame, Ca. 94010, under the trademark ORALASTIC. This material is nearly odorless, tasteless and translucent and remains dimensionally stable while retaining its memory indefinitely. Its clarity allows one to clinically detect any tissue impingement that might occur and to observe the tooth progressively settle into the positioner tooth sockets or impressions.

The body 12 is of integral construction and includes an upper portion 14 of U cross section and a lower portion 16 of inverted U cross section, the bights of the U-shaped upper and lower portions 14 and 16 being in abutting merging relation, with the inner edge 18 and outer edge 20 forming an upper trough 22 and a lower trough (not shown). The inside of the upper trough 22 is formed with teeth impressions or sockets 24 which correspond to the teeth of the wearer disposed in predetermined ultimate positions of movement. Similarly, the lower trough is formed with teeth impressions or sockets of the lower teeth of an intended wearer disposed in predetermined ultimate positions of movement. The depths of the upper portion 14 and the lower portion 16 are greater than the depths of the upper and lower teeth of the intended user so that portions are provided fitting over the gums of the wearer.

Figure 2:
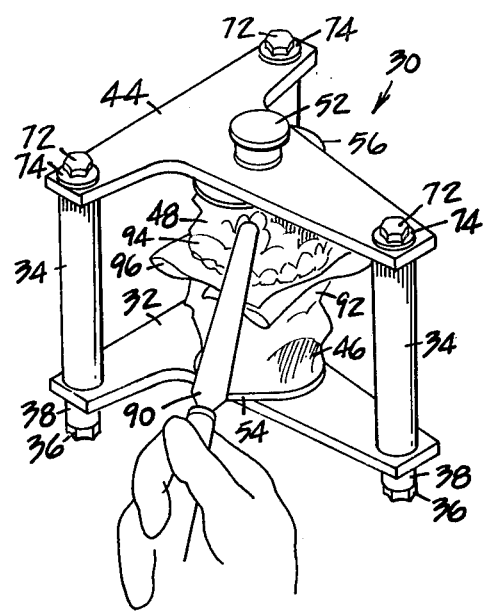
FIG. 2 is a perspective view showing the upper model being mounted to the correlator in the interocclusal record position.

The novel centric correlator generally indicated 30 of the present invention is illustrated in FIGS. 1, 2 and 3. The correlator 30 has a lower frame member 32 somewhat "T-shaped" in configuration having a plurality of perpendicular posts 34 upstanding therefrom. As shown in FIG. 6, each post 34 is held in place by bolt 36 which is inserted through identical hollow spacer member 38 and lower frame aperture 40 to threadably engage internal post threads 42. Upper frame member 44 has the same "T-shaped" configuration as lower frame member 32. It should, however, be understood that the frame members 32 and 44 could have any number of compatible configurations.

Supported at about the mid-portion of each of frame member 32 and 44 are set-up models 46 and 48, respectively. The set-up models 46 and 48 are secured to their respective frames by thumb screws 50 (FIG. 4) and 52 which are attached to locking studs that project through frame members 32 and 44 into threaded engagement with bores in plates 54 and 56. As seen in FIG. 1, plate 56 has bore 58 therein and protrusions 60 which become embedded in the plaster portion of the set-up model.

Each post 34 terminates in level section 62 joining a bevel section 64 joining the reduced top portion or tip 66. As shown in FIG. 1, the upper frame member 44 has an aperture 68 aligned and sized to fit over the tip 66. Each aperture 68 has a bevel section 70 and level section 71 (FIG. 6) which mate with sections 64 and 62, respectively, of the post 34. To ensure a proper fit the total angle of each pair of aligned bevel sections 64 and 70 should be 90° and as shown in the drawings each bevel is 45°. Bolt 72 having washer 74 thereon engages upper internal threads 76 to lock the upper frame member 44 in place on the posts 34 in a closed position free from all torque, twisting and bending.

Figure 7:
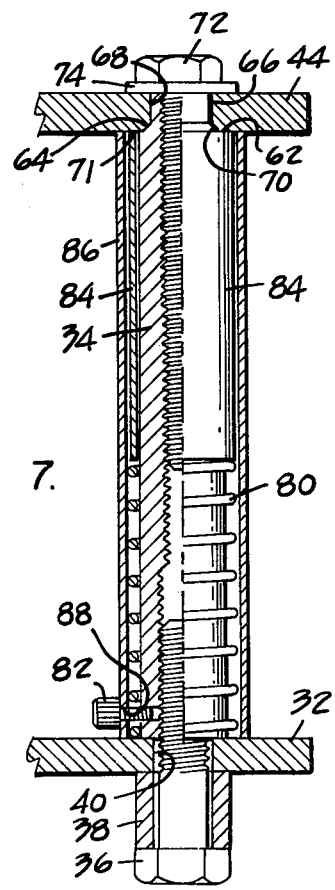
FIG. 7 is a sectional view of a modification of the posts showing a coil spring therein.

FIG. 7 illustrates a modification of post 34 wherein coil spring 80 surrounds the lower part of post 34 and is kept in place by set screw 82. Spring 80 pushes upward against sleeve 84 which surrounds the upper part of post 34 to elevate upper frame member 44 above posts 34 when the bolts 72 are not threadably engaged therein. Cover 86 surrounds spring 80 and sleeve 84 and has a suitable opening 88 for set screw 82.

The present novel method of forming the tooth positioner 10 with the correlator 30 involves the initial step of preparing proper set-up models mounted to an articular, an item of dental equipment employed to simulate mandible movements, the operation of which is well-known in the art. The articulator incisal guide pin is raised to the minimum opening necessary to allow for the thickness of the positioning material interocclusally, taking into consideration the necessity of providing air ducts for mouth breathing patients. It is extremely important that the tooth positioner be constructed at the terminal hinge of the patient. If the amount of positioner material between the occlusal surfaces of the teeth is different from what a true opening of the joint would require, then the tooth positioner loses its accuracy.

Once the incisal guide pin has been set to provide vertidcal space between the teeth equal to the thickness of the tooth positioner, an interocclusal record is taken from the set-up models in the opened position with the articulator locked in centric. A sheet of beauty pink extra base plate wax or the like is rolled over into about four thicknesses, softened in a water bath of about 130°–140°F. and placed between the teeth on the opposing set-up models. (Of course, any suitable material capable of securing an accurate centric relation interocclusal record may be used.) The articulator is then closed until the incisal guide pin touches the incisal guide table to provide the predetermined opening. The material is allowed to set, which setting can be hastened by using cold tap water. However, care must be exercised not to remove the material before it has set properly, to avoid distortion.

After the interocclusal record has set, it can be removed from between the teeth. It is this interocclusal record which will orient the duplicated set-up models for construction of the tooth positioner. The set-up models are then removed from the articulator and duplicted in a manner well-known in the art. An impression is taken of the upper and lower models with alginate using rim-lock impression trays. These are then poured in a hard white stone, trimmed on a grinder close to the depth of the muccobuccal fold. The bubbles are removed and the gingival contour is accentuated by carving. A finishing line is then marked with a red pentel to aid in the packing and trimming of the tooth positioner material.

As shown in FIG. 1, some mounting plaster or stone is placed on lower plate 54 by means of spatula 90 and the lower ground model 92 is mounted thereon and centered between the upper 44 and lower 32 frame members of the correlator 30 conveniently to allow for closure of the upper ground model 94 later. Models 92 and 94 are mounted in much the same fashion as one mounts models on an articulator. Once the mounting plaster or stone has set, the centric interocclusal record 96 taken of the set-up on the articulator is placed on the lower model 92. As shown in FIG. 2, the upper model 94 is placed into the interocclusal record 96 and attached by means of spatula 90 to upper plate 56 which is secured by thumb screw 52 to upper frame member 44. While the plaster or stone on the upper model 94 is still soft, the correlator 30 is closed to its centric position and bolted shut (FIG. 2) by rotating bolts 72 all the way down until the bevel portions 64 and 70 are in pressing relationship. The soft plaster or stone is then smoothed and allowed to set. With the models 92 and 94 indexed into the interocclusal record 96, the correlator 30 has captured the exact interocclusal relationship of the set-up models on the articulator. Likewise, this exact interocclusal relationship can be recaptured after the interocclusal record 96 is removed and the tooth positioner material 98 (FIG. 3) is packed between the teeth for processing.

Once the upper mounting paster or stone is set, the bolts 72 can be unscrewed so that the upper frame member 44 can be raised to allow for removal of the centric interocclusal record and placement of the positioner material. The modification of the post shown in FIG. 7 automatically elevates upper frame member 44 as the bolts 72 are unscrewed because of the force spring 80 applies to sleeve 84.

The material 98 is placed over the occlusal surfaces of the lower teeth, making certain that the teeth fit well into the wedge shape of the material. The upper frame member 44 can then be slowly closed, again making certain that the teeth fit into the wedge shape of the material 98. The correlator 30 is then bolted shut by bolts 72 to its centric position, thereby maintaining the same exact centric relation distance between the teeth that was obtained with the centric interocclusal record 96.

At this point, a sheet of polyethylene material can be stretched and placed over the labial surface of the material 98 and it can then be molded with finger pressure into the desired shape of the positioner. The lingual surfaces can be adapted to the model by moistening the fingers and molding to the proper thickness.

Any unwanted bulk or thickness can be removed by simply lifting the polyethylene and cutting with an ordinary table knife along the red pentel finishing line. This may expose a thickness in the posterior area, so the above process can be repeated until the desired shape and thickness are achieved.

When the packing and shaping has been completed, the polyethylene material is removed and the correlator 30 is immersed into a pot 100 of boiling water 102 and is allowed to boil for a period of 45 minutes until cured (FIG. 4). If a firmer positioner is desired, boil for a longer period of time. The material is processed or cured when it is possible to see the teeth therethrough.

After curing the correlator 30 is opened in the usual manner and the tooth positioner 10 is removed, trimmed and polished. The finished tooth positioner 10 can then be placed on the upper set-up model on the articulator and you should be able to hinge the articulator closed so the teeth fit directly into the positioner 10 and allow the incisal guide pin to touch the incisal guide table with the condyles seated. This is a check to verify that one has constructed the positioner 10 on the hinge-axis of the mounting.

It is thus readily apparent that there has been provided a unique centric correlator for forming a tooth positioner, and a novel method forming the accurate hinge axis tooth positioner which fulfill all of the objects and advantages sought in respect to each.

It will be obvious that numerous modifications and variations are possible for the above described apparatus for and method of forming accurate hinge axis tooth positioners within the scope of the present invention. The foregoing description, as setting forth various constructional and operational details for purposes of understanding only, is not to be taken as limiting the scope of the present invention which is defined only by the following claims.

I claim:

1. A method of constructing an accurate hinge axis tooth positioner comprising:
   (a) preparing models of the upper and lower teeth of a patient with the teeth relocated to predetermined positions;
   (b) taking a centric interocclusal record of the prepared models mounted on an articulator in the centric relation but spaced apart the thickness of the tooth positioner material;
   (c) duplicating the said models;
   (d) mounting said duplicated models on a correlator in indexed engagement with said interocclusal record;
   (e) removing said interocclusal record from between said duplicated models;
   (f) disposing resilient deformable material between said duplicated models;
   (g) returning said duplicated models to the established interocclusal record position forming impressions of the upper and lower teeth in said material; and
   (h) curing said material through the application of heat to provide an accurate hinge axis tooth positioner.

2. The method of claim 1 wherein the material is cured by immersion into boiling water for about 45 minutes.

3. A correlator for reproducing onto a tooth positioner material the exact centric interocclusal record taken from opposing set-up models mounted on an articulator comprising:
   (a) a lower frame member having a plurality of perpendicular posts upstanding therefrom, each post having a reduced top portion;
   (b) an upper frame member having aligned apertures sized to fit over said posts;
   (c) means on said frame members for securing opposing set-up models thereto;
   (d) bevel cooperating means on said posts and on the underside of said upper frame member for positioning said upper frame member onto said posts; and
   (e) tightening means on said posts for locking said upper frame member in place on said posts whereby all torque, twisting and bending is eliminated and the exact centric interocclusal record taken from opposing set-up models can be reproduced onto a tooth positioner material.

4. The correlator of claim 3 wherein spring means on said posts bias the upper frame member away from the lower frame member.

* * * * *